United States Patent [19]

Esmon et al.

[11] Patent Number: 5,147,638

[45] Date of Patent: Sep. 15, 1992

[54] INHIBITION OF TUMOR GROWTH BY BLOCKADE OF THE PROTEIN C SYSTEM

[75] Inventors: Charles T. Esmon; Philip C. Comp, both of Oklahoma City, Okla.

[73] Assignee: Oklahoma Medical Research Foundation, Oklahoma City, Okla.

[21] Appl. No.: 389,617

[22] Filed: Aug. 4, 1989

Related U.S. Application Data

[63] Continuation-in-part of Ser. No. 292,447, Dec. 30, 1988, abandoned.

[51] Int. Cl.⁵ .................... A61K 37/00; A61K 37/66; A61K 39/00

[52] U.S. Cl. .................... 424/85.8; 424/85.1; 424/85.2; 424/85.4; 424/85.5; 435/212; 514/2; 514/8; 514/12; 530/351; 530/381; 530/388.25; 530/389.3

[58] Field of Search .................... 424/85.1, 85.2, 85.5, 424/85.8; 514/2, 12; 530/387

[56] References Cited

U.S. PATENT DOCUMENTS

| | | | |
|---|---|---|---|
| 4,650,674 | 3/1987 | Aggarwal et al. | 424/85.5 |
| 4,677,064 | 6/1987 | Mark et al. | 435/69.51 |
| 4,775,624 | 10/1988 | Bang et al. | 435/226 |

FOREIGN PATENT DOCUMENTS 280135 8/1988 European Pat. Off.

OTHER PUBLICATIONS

Cannistra et al. (1987) J. Clin. Invest 79, 1720–1728.
Suzuki et al. (1984) J. Biochem. 95, 187–195.
Nawroth et al. (1986) J. Exp. Med. 163, 740–745.
Dahlback (1986) J. Biol. Chem. 261, 12022–12027.
Suzuki et al., J. Biochem., 97(1), 127–138 (Jan. 1985).
Nussenzweig and Melton, *Methods in Enzymology,* 80, 124–133 (1981).
Laurell et al., *FEBS Letters,* 191(1), 75–81 (Oct. 1985).
Ohlin and Stenflo, J. Biol. Chem., 262(28), 13798–13804 (Oct. 5, 1987).
Dahlback, *Biochem. J.,* 209, 837–846 (1983).
Liao et al., Cancer *Immunol. Immunother.* 28(1), 77–86 (1989).
Avner et al., *J. Biol. Response Modifiers,* 8(1), 25–36 (1989).

*Primary Examiner*—Robert A. Wax
*Assistant Examiner*—R. Keith Baker
*Attorney, Agent, or Firm*—Kilpatrick & Cody

[57] ABSTRACT

Compositions, and methods of use thereof, for the inhibition of tumor growth and killing of tumors having extensive microcirculation wherein the active agent is a compound blocking the Protein C system, preferably anti-Protein C antibody, anti-Protein S antibody, and C4b binding protein. In the most preferred embodiment, the Protein C blocking compound is provided in combination with a cytokine such as tumor necrosis factor (TNF), gamma interferon, interleukin-1, interleukin-2 and granulocyte-macrophage colony stimulating factor. Examples are provided demonstrating the administration of the Protein C blocking compound, alone or in combination with TNF, to dogs having canine veneral tumors, or fibrosarcoma, and an adenocarcinoma, and pigs with melanoma followed by significant tumor reduction.

29 Claims, 3 Drawing Sheets

Necrotic Remains of Tumor

INHIBITION OF TUMOR GROWTH BY BLOCKADE OF THE PROTEIN C SYSTEM

This is a continuation-in-part of U.S. Ser. 07/292,447 entitled "Monoclonal Antibody Against Protein C" filed Dec. 30, 1988 by Charles T. Esmon and Naomi L. Esmon, now abandoned.

BACKGROUND OF THE INVENTION

This is generally in the area of compositions for treatment of cancer, in particular, compositions containing blockers of the protein C system in combination with a lymphokine.

A variety of mechanisms in tumors capable of promoting clot formation have been described (Dvorak, H. F. *Human Path.* 18,275-284 (1987); Rickles, F. R., Hancock, W. W., Edwards, R. L., et al. *Sem.Thromb. .Hemost.* 14,88-94 (1988)). Initially, the discovery of extravascular fibrin deposits in a variety of animal and human tumors prompted the search for these tumor-associated clotting mechanisms. This extravascular fibrin disposition has been found in association with prothrombin, factor VII and factor X in certain tumor cells in situ by immunohistochemical techniques. A heat- and acid-stable glycoprotein present in mucin produced by certain adenocarcinomas is capable of catalyzing the conversion of factor X to factor $X_a$. A 68,000 dalton cysteine protease has been identified in a number of tumor lines which activates factor X, independent of the actions of factor $VII_a$ and tissue factor. Some tumor homogenates display tissue factor activity, while other tumor cell lines have cell membranes with receptors for factor $V_a$ and are capable of catalyzing the conversion of prothrombin to thrombin. Abnormalities in coagulation parameters observed in certain cancer patients has prompted the hypothesis that tumor-associated clotting may be o sufficient magnitude to cause systemic activation of the clotting system.

Alterations in the fibrinolytic system are observed in tumors and transformed cells. Plasminogen activator activity has been found to be higher in extracts of surgically excised human cancer tissues than in surrounding benign tissue. In addition to other possible roles for plasminogen activator, such as participation in tumor invasion of normal tissue, this suggests that tumors have the capacity to promote fibrin degradation. Urokinase-type plasminogen activator appears to be produced by tumors with greater frequency than tissue-type plasminogen activator. It is not known if the production of plasminogen activators by tumors is involved in preventing thrombus accumulation within the bed of the tumor.

Protein C is a vitamin K-dependent plasma protein. Activated protein C serves as a natural anticoagulant by inhibiting the clotting cascade at the levels of factor $V_a$ and factor $VIII_a$ (Walker, F. J., Sexton, P. W. and Esmon, C. T. *Biochim.Biphys.Acta* 571,333-342 (1979); Fulcher, C. A., Gardiner, J. E., Griffin, J. H., et al. *Blood* 63,86-49 (1984)). Protein C is rapidly converted to activated protein C by a complex of thrombin and the endothelial cell surface protein, thrombomodulin. Thrombomodulin forms a 1:1 stoichiometrio complex with thrombin and increases the rate at which thrombin activates protein C by approximately 20,000-fold. This activation occurs primarily in the capillaries, where the availability of a large endothelial surface area per unit of plasma volume favors complex formation between thrombin and thrombomodulin. The activation of protein C in the microvasculature forms a potential feedback loop which, when thrombin is formed in the circulation, generates activated protein C. The activated protein C in turn inhibits further thrombin formation. This has been demonstrated directly in dogs, where low level intravenous thrombin infusion results in the generation of activated protein C and anticoagulation of the animal. A more complete review of the roles of thrombomodulin and protein C in regulation of blood coagulation is by C. T. Esmon, in *J. Biol. Chem.* 264(9), 4743-4746 (1989).

Thrombomodulin has been identified on a variety of cultured endothelial cell lines and on the luminal surface of blood vessels (Esmon, N. L. *Semin.Thromb. .Hemost.* 13,454-463 (1987)). Thrombomodulin has also been identified by functional and immunochemical means on tumor cells, including human lung carcinoma -line CL-185 and Bowes melanoma cells (Marks, C. A., Bank, N. U., Mattler, L. E., et al. *Thromb.Hemost.* 54,119 (1985)), A549 human lung cancer cells (Maruyama, I. and Majerus, P. W. *Blood* 69, 1481-144 (1987)), and angiosarcomas (Yonezawa, S., Maruyama, I., Sakae, K., et al. *Am.J.Clin.Pathol.* 88,405-11 (1987)). The functional role of thrombomodulin on the tumor cells is subject to speculation. Tumor associated thrombomodulin may help to protect the tumor from excess fibrin formation. If the protein C-thrombomodulin system is involved in determining the hemostatic balance in the tumor vasculature, blocking protein C activation may shift the hemostatic balance and result in thrombosis of tumor vessels.

In addition to functioning as an anticoagulant, activated protein C promotes fibrinolysis. This action involves complex formation between activated protein C and two inhibitors of plasminogen activator, plasminogen activator inhibitor 1 (PAI-I) and plasminogen activator inhibitor 3 (PAI-3). Complex formation between activated protein C and PAI-1 or PAI-3 may serve to protect plasminogen activators from inhibition and can thus potentially result in an increase in fibrinolytic activity. The extent to which in vivo protein C influences fibrinolytic activity in the body or in tumor beds in particular is unknown.

Protein S, another vitamin K-dependent plasma protein, serves as a cofactor for the anticoagulant and fibrinolytic effects of activated protein C (Walker, F. J. *Semin. Thromb. Hemost.* 10,131-138 (1984); de Fouw, N. J., Haverkate, F., Bertina, R. M., et al. *Blood* 67, 1189-1192 (1986). Protein S exists in two forms in plasma. Forty percent of the protein S is free and serves as a cofactor for activated protein C, and 60% is in complex with C4b binding protein and is functionally inactive. C4b binding protein is an acute phase protein (Boerger, L. M., Morris, P. C., Thurnau, G. R., et al. *Blood* 69,692-694 (1987); Dahlblack, B. *J.Biol.Chem.* 261,12022-12027 (1986)) and thus inflammation, by elevating the levels of C4 binding protein, may shift protein S to the inactive form by the law of mass action. This shift in protein S status may predispose to thrombosis. Hereditary protein S deficiency, at least in some kindreds, is linked to an increased risk of venous thrombosis. See, for example, P. C. Comp, et al., *J. Clin. Invest.* 74, 2082-2088 (1984).

While heterozygous protein C deficiency in certain kindreds is also associated with an increased risk of venous thrombosis, two other protein C deficiency states are characterized by tissue necrosis: homozygous protein C deficiency and the coumarin-induced skin necrosis observed in heterozygous protein C deficient individuals after the initiation of coumarin therapy. In homozygous deficient individuals, skin necrosis occurs on the first or second day of life, resulting in a clinical condition termed purpura fulminans neonatalis. Thrombosis of the small vessels of the skin is characteristic, leading to loss of large areas of skin, which is often fatal. Major vessel thrombosis is also possible.

When oral anticoagulant therapy is initiated in heterozygous protein C deficient patients, extensive microvascular thrombosis may occur. The skin is again the primary target and extensive loss of skin and underlying tissue can occur. The postulated mechanism is a rapid fall in protein C levels in the heterozygous deficient individuals before the levels of clotting factors with a long half-life, such as prothrombin and factor IX, decrease to levels adequate for systemic anticoagulation. A transient hypercoagulable state may exist in these individuals and it is during this period that the tissue necrosis occurs.

Heterozygous protein C deficiency is relatively common in the population and may occur as frequently as 1 in 300 individuals. Coumarin necrosis is rare and this suggests that factors other than protein C deficiency alone must be present. A review of the literature indicates that most patients developing necrosis have some inflammatory condition as well such as an infection, recent surgery or extensive venous thrombi. These accompanying inflammatory changes could decrease thrombomodulin expression, increase tissue factor expression and favor a shift of free protein S to the inactive C4b binding protein-protein S complex. These events would further down regulate the protein C system and promote microvascular clot formation, suggesting that protein C deficiency accompanied by inflammation can result in tissue necrosis.

Although spontaneous regression of solid tumors can occur on rare occasions following febrile illnesses, Dr. William B. Coley demonstrated in *Annals of Surgery* 14,199–220 (1891) that regression of certain solid tumors in humans could follow the administration of heat killed bacteria. The response of the tumors was highly variable and the diagnosis of the tumor type was not always made by histologic examination. However, some of the patients treated with Coley's toxins had long term tumor regression and possible cure. Coley's work and that of other investigators testing the effects of bacterial products on animal tumors, led to the discovery of tumor necrosis factor, a 157 amino acid molecule capable of causing tumor necrosis in a number of murine tumors (Old, L. J. *Nature* 30,602–603 (1987); Old, L. J. *Scientific American* 258,59–75 (1988); Gifford, G. E. and Flick, D. A. *Tumor Necrosis Factor and Related Cytotoxins.* edited by Bock, G. and Marsh, J. Chilchester, p. 3–20 (John Wiley and Sons, 1987). Tumor necrosis factor is produced by macrophages in response to endotoxin. Tumor necrosis factor triggers a number of physiologic responses on skeletal muscle, adipose tissue, endothelium, cartilage, leukocytes and the hypothalamus, and has a direct cytotoxic effect on some tumor cell lines (Tracey, K. J., Lowry, S. F. and Cerami, A. *Tumour Necrosis Factor and Related Cytokines*, p. 88–108 (1987).

Tumor necrosis factor causes inflammatory changes at the endothelial level by increasing the adhesion of PMNs, blood monocytes and related leukocyte cell lines. This may result from the tumor necrosis factor induced production of endothelial-leukocyte adhesion molecules (E-LAMs) by the endothelium (Pober, J. S., Bevilacqua, M. P., Mendrick, D. L., et al. *J.Immunol.* 136,1680–1687 (1986); Pober, J. S., Lapierre, L. A., Stolpen, A. H., et al. J.Immunol. 138,3319–3324 (1987); Bevilacqua, M. P. and Gimbrone Jr., M. A. *Sem.-Thromb.Hemost.* 13,425–433 (1987). Tumor necrosis factor also stimulates endothelial cell production of platelet activating factor which may also promote microvascular thrombosis by platelet activation and activation of adherent polymorphonuclear leukocytes (Pober, J. S. *Tumour Necrosis Factor and Related Cytokines* p. 170–184 (1987).

The effects of tumor necrosis factor on the endothelium include increased tissue factor activity and decreased thrombomodulin expression (Moore, K., Esmon C. T., and Esmon, V. L. N. L., et al. *Blood* 79, 124–130 (1987). Tumor necrosis factor and interleukin-1 can decrease the production by human cultured umbilical vein endothelial cells of tissue-type plasminogen activator and increase the production of plasminogen activator inhibitor type 1 (Schleef, R. R., Bevilacqua, M. P., Sawdey, Mr., et al. *J.Biol.Chem.* 263,5797–5803 (1988); Nachman, R. L., Hajjar, K. A., Silverstein, R. L., et al. *J.Exp.Med.* 163,1595–1600 (1986); Emeis, J. J. and Kooistra, T. *J.Exp.Med.* 163,1260–1266 (1980); Bevilacqua, M. P., Schleef, R. R., Gimbrone, M. A., Jr., et al. *J.Clin.Invest.* 78,587–591 (1986). These findings, coupled with the microvascular thrombosis observed in certain protein C deficiency states, suggest that simultaneous administration of tumor necrosis factor and inhibition of the protein C system in vivo may result in intravascular thrombosis.

There is evidence that activated protein C influences the production of TNF in the intact animal. The administration of activated protein C protects against shock induced by the infusion of *E. coli*, as described in U.S. Ser. No. 07/139,922 entitled "Treatment of Dysfunctional Vascular Endothelium Using Activated Protein C" filed Dec. 31, 1987 by Fletcher B. Taylor Jr and Charles T. Esmon. In the animals receiving activated protein C, the production of tumor necrosis factor in response to the *E. coli* is markedly reduced, raising the possibility that blockade of protein C activation in vivo could result in enhanced production of TNF by macrophages or natural killer cells in the tumor bed in the presence of low levels of endotoxin. This could in turn contribute to further toxic effects on the tumor.

Palladino, et al., in *J.Immunol.* 138,4023–4032 (1987); *Tumour NeCrosis Factor and Related Cytokines*, p. 21–38 (1987); has proposed that injection of tumor necrosis factor into Meth A sarcoma bearing mice actually causes a series of events which result in tumor rejection: 1) hemorrhagic tumor necrosis, initiated in the first one to four hours involving PMN activation and their localization to the tumor; 2) direct cytostatic/cytotoxic effects on the tumor as growth stops, at 24 to 72 hours; and 3) a specific T-cell mediated immune response to the tumor, at two to four weeks. Blockade of the protein C system may potentiate certain aspects of the TNF mediated necrosis in addition to promoting microvascular thrombosis. Blockade of the protein C system should result in increased thrombin generation by tissue factor at the endothelial surface. The thrombin which is produced can increase endothelial cell production of platelet activating factor, which would prime marginated granulocytes and thus enhance the PMN mediated endothelial cell injury.

Anticoagulants block the Shwartzman reaction, presumably by preventing fibrin deposition and microvascular thrombosis (Edwards, R. L. and Rickles, F. R. Science 200, 541-543 (1978). If tumor killing by tumor necrosis factor does have characteristics in common with the Shwartzman reaction, blocking protein C activation could allow intravascular thrombosis to proceed unimpeded and increase the extent and severity of damage to the microvasculature, and thus increase tumor killing. Since the use of tumor necrosis factor in the treatment of human malignancies is accompanied by serious side effects, protein C blockade, which may potentiate the tumor-directed effects of a given dose of tumor necrosis factor, should be worth investigation.

It is therefore an object of the present invention to provide a method and compositions to block the natural anticoagulant pathways, to thereby promote microvascular coagulation in the new capillaries growing into tumors and by so doing block the process of angiogenesis.

It is a further object of the present invention to provide a method and compositions to promote an immune response against tumors by blocking the natural anticoagulant pathways.

SUMMARY OF THE INVENTION

Compositions, and methods of use thereof, for the inhibition of tumor growth and killing of tumors having extensive microcirculation wherein the active agent is a compound blocking the Protein C system, preferably anti-Protein C or anti-activated Protein C antibody, anti-Protein S antibody, inactivated activated Protein C, and C4b binding protein, administered systemically or at the site of the tumor. In the most preferred embodiment, the Protein C blocking compound is provided in combination with a cytokine that stimulates natural killer and lymphokine-activated killer cell-mediated cytotoxicity, activates macrophages, stimulates Fc receptor expression on mononuclear cells and antibody-dependent cellular cytotoxicity, enhances HLA class II antigen expression, and/or stimulates procoagulant activity, such as tumor necrosis factor (TNF), gamma interferon, granulocyte-macrophage colony stimulating factor, interleukin-1 or interleukin-2. It is possible to stop or reverse the hypercoagulapathy following administration of the Protein C blocking compound by administration of an agent inhibiting the blocking compound, such as by administration of Protein C, or more preferably activated Protein C, when the blocking compound is anti-Protein C antibody. Although initial studies show that a single treatment is effective in significantly reducing tumor size, different Protein C blocking compounds, alone or in combination with different cytokines and/or other anti-tumor agents, such as chemotherapeutic agents or anti-tumor monoclonal antibodies, can be administered simultaneously or subsequently to the initial treatment to reduce tumor size. Radiation and hyperphermia can also be used to sensitize the tumor to the protein C blocking agent.

Examples are provided demonstrating the systemic and local administration of the Protein C blocking compound, alone or in combination with TNF, to dogs having canine venereal tumors, a fibrosarcoma, and an adenocarcinoma, and to pigs having melanomas, followed by significant tumor reduction. Administration of the composition to a dog with a lymphoma was not effective.

DETAILED DESCRIPTION OF THE INVENTION

Blockage of the natural anticoagulant pathways, in particular the protein C pathway, uses the natural procoagulant properties of the tumor to target the tumor capillaries for microvascular thrombosis, leading to hemorrhagic necrosis of the tumor. This method provides a new approach to the treatment of solid tumors either alone or in conjunction with biological response modifiers, chemotherapy or radiation treatments.

Tumors contain proteins which predispose to the formation of blood clots in the vessels in the tumor bed. Tumors also contain other proteins and cellular elements which prevent thrombosis of tumor blood vessels. Tumor necrosis results from altering the hemostatic balance between procoagulant and anticoagulant mechanisms to favor thrombosis of the tumor microvasculature. The hemostatic balance of the tumor can be altered by blocking the conversion of protein C to its active form (activated protein C). The procoagulant mechanisms present in the tumor bed will then function without opposition and cause thrombosis of the tumor vessels.

The protein C cascade can be inhibited directly and specifically by several means, including antibodies to Protein C or activated Protein C, antibodies to Protein S, inactivated Protein C and C4b binding protein. The preferred embodiment of the method uses a monoclonal antibody to human protein C. In the most preferred embodiment, a monoclonal antibody known as HPC4, described in U.S. Ser. No. 07/292,447 entitled "Monoclonal Antibody Against Protein C" by Charles T. Esmon and Naomi L. Esmon. The epitope for this antibody spans the activation site in protein C and as a result blocks protein C activation. As an experimental tool it is important to note that the antibody cross reacts with protein C from canine, porcine and at least two primate plasmas, baboon and marmoset. It does not cross react with bovine or mouse protein C. The inhibitory effect can be reversed instantly by administration of activated protein C to which the antibody does not bind. The antibody therefore provides a means to selectively inhibit the protein C pathway in vivo and to reverse the process if thrombotic complications ensue at sites other than the tumor. Other antibodies to Protein C and activated Protein C are known, for example, the antibodies described by Ohlin and Stenflo in *J. Biol. Chem.* 262(28), 13798-13804 (1987); Laurell, et al., FEBS Lett 191(1), 75-81 (1985); and Suzuki, et al., J. Biochem. (Tokyo) 97(1), 127-138 (1985).

Antibodies to Protein S can be obtained using methodology known to those skilled in the art for the preparation of hybridomas from animals immunized against Protein S purified using the method of Comp, et al., in J. Clin. Invest. 74, 2082-2088 (1984).

Blocking protein C activation in vivo in the dog for 18-30 hours does not result in infarction of body organs nor does it result in detectable skin neorosis, which is observed in homozygous protein C deficient newborn infants. However, the potential risk of thrombotic complications outside the tumor vasculature is a consideration with any blockade of the protein C system, whether congenital or induced by a specific monoclonal antibody. An alternative method for blocking the Protein C system, possibly with less risk of systemic thrombosis, involves blocking protein S function. Blocking protein S function may be tolerated without the development of major thrombotic side effects, such as thrombophlebitis. During pregnancy an acquired protein S deficiency occurs and protein S activity drops to 38% +/−17% (mean +/−1 S.D.). Thrombotic complications occur rarely during pregnancy, suggesting that protein S deficiency is tolerated in many individuals without severe clotting.

Protein S activity is blocked in vivo with specific monoclonal antibodies against human protein S. The monoclonals which inhibit protein S function block protein S in vivo. The monoclonals which bind protein S, but do not block function, should not block the system. The administration of the blocking monoclonals is anticipated to decrease tumor growth and/or cause regression, whereas the non-inhibitory antibodies should not.

In the most preferred embodiment, monoclonal antibodies of the same species as the patient to be treated are used. Since a single dose may be effective, however, it is possible to administer cross-species antibodies and still see tumor reduction. The antibody binding region can also be cloned and recombinantly expressed, using methods known to those skilled in the art, for using in blocking the protein C pathway.

A second approach to blockade of the protein C system does not involve the use of monoclonal antibodies. C4b binding protein can be purified and infused at high levels. C4b binding protein in vivo should result in a shift in protein S from the free, and functionally active, form to the inactive C4b binding protein-protein S complex, rendering the protein C system inactive.

Human plasma contains free and bound protein S. C4b binding protein can be purified using affinity chromatography with a monoclonal antibody directed against the human C4b binding protein. C4b binding protein (C4bBP) can be obtained using the method of Dahlback, Biochem. J. 209, 847-856 (1983) or Nussenzweig, et al., Methods Enzymol. 80, 124-133 (1981). Methods yielding high levels of C4b binding protein are as follows.

A method for purification of C4b binding protein is as follows: 30 liters of plasma is thawed at 37° C. and 10,000 units porcine heparin added with stirring. The plasma is diluted with an equal volume of 10 mM benzamidine HCl, 0.02% NaN3, 2 mM ethylenediaminetetraacetic acid (EDTA), and 0.8 units heparin/ml in 20 mM Tris buffer, pH 7.5. The diluted plasma is then batch adsorbed with gentle stirring for 1 hr with 30 gm QAE-Sephadex TM (Pharma Chemicals Piscataway, N.J.) which has been rehydrated in ° mM Tris buffer, pH 7.5 containing 0.1M NaCl, 5 mM benzamidine HCl, and 0.02% sodium azide. The QAE-Sephadex is allowed to settle for 45 min and the supernatant siphoned off. The resin is then packed in a 10×30 cm column and washed with 1 L 150 mM NaCl, 10 mM benzamidine HCl, in 20 mM Tris buffer, pH 7.5. The column is step eluted with 1 L 20 mM Tris, pH 7.5 buffer containing 0.5M NaCl, 10 mM benzamidine HCl, and 0.02% sodium azide. The eluted material is made 1 mM in diisopropylfluorophosphate and 10,000 units heparin added. Ammoniumsulfate is added to the supernatant to 30% saturation at 4° C. and held at that temperature with gentle stirring for 1 hour. Following precipitation, the pellet is resuspended and de salted into 20 mM Tris buffer, pH 7.5, containing 0.1M NaCl and 5 mM benzamidine HCl. The desalted material is then loaded onto a 2.5×5 cm column of a monoclonal antibody directed against C4b-binding protein linked to Affigel 10 TM (Pharmacia) (5 mg antibody/ml gel) The column is eluted with 80% ethylene glycol in 1 mM MOPS buffer, pH 7.5, at room temperature at 10 ml/hr or with distilled water containing 1 mM MOPS, pH 7.5, and applied to a heparin agarose column as described below.

Protein S can simultaneously be isolated from the plasma and the C4bBP-protein S complex by QAE adsorption and elution of the plasma before adsorption with the monoclonal antibodies. This allows isolation of both the free protein S and the C4bBP protein S complex, as well as protein C and some other plasma factors. The QAE eluate is prepared by diluting 30 L of human plasma 1:1 with 0.02 Tris HCl, pH 7.5, 10 mM benzamidine HCl, 1 unit/ml heparin, and adsorbing for one hr with 30 g of preswollen QAE Sephadex TM . The QAE is allowed to settle for 30 min, the supernatant is decanted or siphoned off and the QAE packed into a 10 cm diameter column, washed with approximately two liters of 0.15M NaCl in the Tris buffer and eluted with 0.5M NaCl. This eluate, which is a bright green color, is adsorbed for one hr with anti-C4bBP antibody BP45 to remove the C4bBP and C4bBP-protein S complex and then for one hr with the $Ca^{2+}$ dependent anti-Protein S antibody S163 to remove free protein S. The BP45 column is then processed and protein S and C4bBP recovered as described below. The yield of protein S from the S163 is about 10 mg, the yield of C46BP is about 50-100 mg and yield of protein S from the complex is about 10 mg.

A variation of the method for isolating C4bBP in high yield is described below. Three liters of frozen plasma are thawed at 37 C., made 10 mM in benzamidine HCl (BHCl), and cooled in an ice bath to 4° C. PEG 8000 is added with stirring to 6% wt/vol and stirred for one hr. This is centrifuged at 4000 rpm in the PR6000 for 30 min at 4° C. and the supernatant discarded. The pellet is resuspended in 1 L of 0.3M NaCl, 0.02 Tris 10 mM BHCL, pH 7.5, for 1 hr at 25 C. on a magnetic stirrer. The suspension is then centrifuged for 30 min at 4000 RPM in the PR 6000 at 25° C. The supernatant contains the C4bBP. The pellet is resuspended again, as above for 1 hr, and recentrifuged. This supernatant also contains C4bBP. Small samples of each fraction are assayed for C4bBP. The two fractions are pooled and adsorbed to a BP 45 column for 1 hr at 25° C. The column is washed overnight with 4 L of 0.25 NaCl in 0.02 Tris 10 mM benzamidine HCl (BHCL), then washed with one column volume of 0.1M NaCl in 0.02M Tris to remove the BHCL. The C4bBP is eluted with 80% ethylene glycol, 1 mM MOPS.

The eluate is applied to a heparin agarose column (5×8 cm) medium mesh. Application can be rapid, approximately 20 cm pressure head. The C4bBP binds to the column while the protein S washes through. The column is then sequentially washed with (1) 100 ml of 80% ethylene glycol, (2) 100 ml of 0.1M NaCl, 0.01M MOPS pH 7.5 The C4bBP is then eluted with 1M NaCl, 0.01M MOPS, pH 7.5, using about 1 col volume elution buffer/hr during the elution to keep the C4bBP very concentrated. The yield is about 100 mg from 3 liters plasma with no detectable contaminants by gel electrophoresis.

For purification of protein S, the C4bBP breakthrough from the heparin-agarose column is applied to an S163 column. Since this is a $Ca^{2+}$ dependent monoclonal antibody the sample is made 2 mM in $Ca^{2+}$. The S163 column is washed with 0.1M NaCl, 0.02M Tris HCl pH 7.5 in 2 mM $Ca^{2+}$, and eluted in the above buffer with 2 mM EDTA replacing the $Ca^{2+}$. Yields from this approach are approximately 10 mg protein S that is about 80% uncleaved from 6 liters of plasma.

Pyrogen-depleted C4b binding protein is administered to raise plasma levels 5-fold, which should result in a greater than 90% reduction of free protein S and a corresponding reduction of protein S activity.

The Protein C blocking agent is preferably administered in combination with a cytokine that stimulates natural killer and lymphokine-activated killer cell-mediated cytotoxicity, activates macrophages, stimulates Fc receptor expression on mononuclear cells and antibody-dependent cellular cytotoxicity, enhances HLA class II antigen expression, and/or stimulates procoagulant activity, such as tumor necrosis factor (TNF), interleukin-1 (IL-1), interleukin-2 (IL-2), gamma interferon (gamma-IFN), or granulocyte-macrophage colony stimulating factor (GMCSF). Recombinant TNF, IL-2 and GMCSF can be obtained from Cetus Corporation, 1400 53rd Street, Emeryville, Calif., or Biogen Corp., Cambridge, Mass. IL-I can be obtained can be obtained from Genentech, South San Francisco, Calif., or Hoffman-LaRoche, Nutley, N.J. Gamma interferon can be obtained from Genentech, Biogen or Amgen Biologicals, Thousand Oaks, Calif.

Tumor necrosis factor is capable of producing significant systemic toxicity in humans including fever, chills, anorexia and nausea, hypotension and abnormalities of liver function (Spriggs, D. R., Sherman, M. L., Frei III, E. and Kufe, D. W. *Tumour Necrosis Factor and Related Cytokines*, p. 124–139 (1987). Other monokines may be more suitable for enhancing the tumor directed effects of protein C blockade. For example, interferon-gamma displays a number of properties which suggest that the combination of protein C blockade and interferon-gamma might be successful in tumor killing. These characteristics include stimulation of natural killer and lymphokine-activated killer cell-mediated cytotoxicity, activation of macrophages with in vivo and in vitro stimulation of peroxide generation, stimulation of Fc receptor expression on mononuclear cells and antibody-dependent cellular cytotoxicity, and enhancement of HLA class II antigen expression. Interferon-gamma is relatively well tolerated by human subjects at doses which provide significant immune stimulation.

Another alternative to the use of TNF is gamma irradiation in conjunction with blockade of Protein C activation. Canine tumors are relatively sensitive to X-irradiation and radiation doses of 1000–3000 rads cause complete tumor regression. However, a dose of 100–300 rads delivered to the tumor bed is expected not to kill the tumor but should be sufficient to cause mild local inflammation in the tumor. This inflammation may be sufficient to cause expression of tissue factor and a loss of thrombomodulin expression on endothelial cells in the tumor, which in turn could render the tumors more sensitive to the effects of Protein C blockade.

Hyperthermia can also be used to sensitize cutaneous or subcutaneous tumors to the effects of the protein C blocking agent, alone or in combination with the cytokine. Methods for inducing localized or systemic hypothermia are known to those skilled in the art.

Optionally, other compositions and methods for treatment can be administered simultaneously or subsequently to treatment with the Protein C blocking compound and the cytokine, such as radiation which induces inflammation in the tumor or chemotherapy with an agent such as cis-platinum or 5-fluorouracil (5-FU), which selectively inhibits the most rapidly replicating cells.

The therapeutic regime actually used is dependent on the patient and the type of tumor to be treated. In the preferred embodiment, the Protein C blocking compound and/or cytokine is administered in a single dosage, either systemically or at the site of the tumor. In general, an amount of Protein C blocking compound in excess of the amount of material in the body to be inhibited will be administered with each dose. For example, anti-Protein C antibody is administered in an amount equal to the molar concentration of Protein C in the plasma, or about 10 μg antibody per milliliter of blood (i.e., at approximately a two fold molar excess of protein C binding sites). C4b binding protein is administered in a dosage equal to or greater than five times the plasma level of C4b binding protein.

TNF is administered systemically in a dosage of approximately ten percent of the $LD_{50}$ of 100 μg TNF/kg body weight, or about 10 μg TNF/kg body weight. TNF can be administered into the tumor at a dosage between approximately one microgram and 200 microgram/$m^2$, preferably less than 25 micrograms/$m^2$. TNF is FDA approved for use in cancer patients, however, the toxicity is such that the benefits generally do not justify usage in humans. As discussed by Bartsch, et al., in *Eur. J. Cancer Clin. Oncol.* 25(2), 287–291 (1989), the side effects of intratumor administration of rTNF include chills, fever, anorexia, and fatigue, similarly to systemic rTNF treatment. As reported by Kahn, et al., in *J. Acquir. Immune Defic. Syndr.* 2(3), 217–223 (1989), the maximum intralesional dose tolerated in treatment of AIDS-associated Kaposi's sarcoma was less than 100 micrograms/$m^2$, preferably 25 micrograms/$m^2$. Neither study showed significant clinical usage for rTNF alone in the treatment of tumors.

The monoclonal antibody against protein C is the most preferred protein C blocking agent because the protein C blockade can be reversed immediately by the administration of activated protein C. If an immune response against the antibody arises, secondary treatment can utilize the C4bBP since this would not elicit an immune response. The most preferred cytokine at this time is TNF. Tumors not responding to the combination of the protein C blocking agent and TNF can be challenged with the combination of the protein C blocking agent and interferon, IL-1 or 2, and/or GMCSF. If the tumor is still not completely resolved, the patient can be further treated with monoclonal antibodies against specific tumor antigens, chemotherapeutic agents, and/or radiation.

As discussed above, the hypercoagulable state can be reversed by administration of a compound binding to and inhibiting the Protein C blocking compound, such as the HPC4 anti-protein C epitope peptide or by administration of activated Protein C which does not bind to this antibody. A continuous infusion of 30 μg/kg/min recombinant tissue plasminogen activator can also be used. Based on studies of coronary artery thrombosis in dogs, this dose is anticipated to be sufficient to cause lysis of microvascular clots and decrease the euglobulin clot lysis time by at least 50% during the TPA infusion. The tissue plasminogen activator infusion will be continued over a six-hour period. Heparin may also be useful, although clinical experience with homozygous protein C deficient infants indicates that protein C concentrates, but not heparin, are effective therapeutically.

EXAMPLE 1

Treatment of a transplantable canine venereal tumor using anti-Protein C and TNF.

The anti-Protein C antibody, either with or without added TNF, has been used to block the growth of a transplantable canine venereal tumor. The tumor is an undifferentiated round-cell neoplasm, characterized as a sarcoma, described by R. B. Epstein, et al., in *Neoplasm Immunity: Experimental and Clinical* 299-, Crispen, ed. (Elsevier North Holland, Inc. 1980). TNF causes hemorrhagic necrosis in susceptible tumors in mice. This tumor killing and necrosis was postulated to be secondary to microvascular thrombosis since it is known that TNF down regulates natural anticoagulant activities and elicits the formation of coagulant complexes. However, in most animals, hemorrhagic necrosis is not observed. A compound which blocks the Protein C pathway, such as the anti-Protein C antibody HPC-4, described in U.S. Ser. No. 07/292,446, is used to render an animal hypercoaguable since it blocks protein C activation.

The tumor can be easily transmitted to normal dogs by harvesting fresh tumor from a tumor-bearing dog and, following trypsin treatment of the excised tumor, injecting washed tumor cell suspensions subcutaneously into the recipients. The tumor displays a logarithmic growth pattern. Since the tumor grows directly beneath the skin, tumor volume can easily be measured on a daily basis, using a formula for estimating the volume of a sphere based on the height, width and depth of the tumor. The subcutaneous location facilitates needle biopsy and excision of the tumors. Up to six tumors (three on each side of the back) can be placed on each animal. Approximately one-third of tumor-bearing dogs eventually spontaneously reject the tumor. However, this occurs at 4–6 months of growth, which is beyond the 21 days of growth to 50 days of growth used in the study.

The monoclonal antibody, designated HPC4, used to block protein C activation has been previously used successfully to block protein C activation during *E. coli* infusion induced shock in baboons, as described in U.S. Ser. No. 07/139,922 entitled "Treatment of Dysfunctional Vascular Endothelium Using Activated Protein C" filed Dec. 31, 1987 by Fletcher B. Taylor Jr., and Charles T. Esmon. The antibody is $Ca^{++}$ dependent and blocks the activation of protein C by the thrombin-thrombomodulin complex both in vitro and in vivo by binding the heavy chain of protein C at the activation site. A synthetic peptide which encompasses the activation region (residues 6–17 of the heavy chain) is bound by the antibody in the presence of calcium ions, as further described by Stearns, et al., *J. Biol. Chem.* 263(2), 826–832 (1988).

The binding of the HPC4 antibody to the synthetic peptide has facilitated the purification of the monoclonal antibody from mouse ascites fluid and thus has facilitated studies involving in vivo administration of this antibody to large experimental animals such as baboons and dogs. The half-life of the HPC4 anti-1protein C monoclonal antibody has been determined to be approximately 18 hours. At present, 1.1 grams of the HPC4 monoclonal can be obtained from 200 ml of mouse ascites fluid by affinity chromatography using the immobilized peptide. Affinity chromatography permits extensive washing of the bound antibody and significant reduction in endotoxin levels in the antibody preparations and no detectable contaminating mouse proteins.

The combination of the HPC-4 with TNF was tested in three sets of dogs to see if it would facilitate tumor killing or reduce the rate of growth using a dog model. Transplanted venereal tumors were placed subcutaneously into six dogs, with each dog in the first set receiving four tumors and each in the second group receiving six tumors. Growth was monitored by measuring the size of the tumors as described by Epstein, et al. Two dogs were given TNF alone (10 μg/Kg body weight), two dogs were given HPC-4 alone (20 μg/ml plasma volume), and two were given a combination of both.

All animal work was conducted in a blinded manner to decrease the possibility of observer bias. The tumor-bearing dogs were assigned to the various treatments in a randomized manner. The individual measuring tumor growth was unaware of the particular treatment the various animals were given. The veterinary pathologist performing the autopsies did not know the treatment schedule nor did the pathologist evaluating the light and electron microscopic data.

Figure 1:
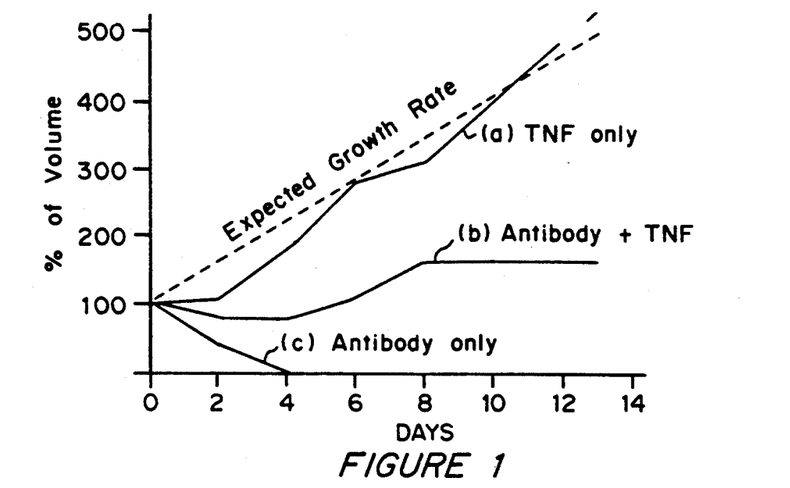
FIG. 1 is a graph of tumor size (% volume) over time (days) following administration of TNF alone (a); anti-Protein C antibody in combination with TNF (b); and anti-Protein C antibody alone (c) to dogs inoculated with the canine veneral tumor.

The results of the first animal study are shown in FIG. 1. Fresh tumor was prepared and injected subcutaneously at six sites on each of three dogs. Twenty-one days later the average volume of the tumors on the animals was approximately 2 ml. An intravenous dose of tumor necrosis factor of 10 μg/kg was selected because although a transient decrease in blood pressure and a transient 40% drop in the white blood cell count occur, the dose is not lethal and is well below the 100 μg/ml dose of TNF found by others to be uniformly toxic in dogs. The anti-protein C monoclonal antibody (HPC4) was administered at a dose of 1 mg antibody/kg, calculated to give plasma levels of approximately 20 μg antibody/ml. In the case of the dog given both the antibody and TNF, the antibody was administered first. The volumes of the tumors (six tumors per dog) were determined by measuring the dimensions of the tumors with calipers. The average tumor volume over time for each of the three dogs is shown in FIG. 1.

By the fourth day, the tumors on the antibody only treated dog were no longer palpable and could not be measured. The tumors on the TNF treated dog grew at a rate comparable to that expected from previous studies on untreated, tumor-bearing animals. This expected growth rate is shown as a dashed line. The tumors in the dog treated with the combination of antibody and TNF demonstrated a reduced rate of growth and had only increased in average volume by 60% when the study was terminated. At autopsy tumors were not found on the dog receiving antibody only. The tumors on the antibody-TNF treated dog were necrotic throughout with few normal tumor cells. Tumors on the TNF treated dogs showed some mild central necrosis only and had large regions of viable tumor cells. Other organs in the animals, including the kidneys, adrenal glands and heart, were examined grossly and by light microscopy and did not show evidence of microvascular thrombosis or vascular damage.

These early tumors usually just cease growing and when administration is at an early stage when the tumor is small, no dramatic effects are noted, although the histology clearly shows hemorrhagic necrosis in the tumor bed within two to six hours of the administration of the antibody with or without the TNF. In one dog with a set of large tumors, about the size of tennis balls, administration of HPC4 resulted in the tumors becoming inflamed, soft and ultimately rupturing. All of these tumors ultimately necrosed. The dog showed few side effects of the treatment and did not seem to be in any obvious discomfort.

Figure 2:
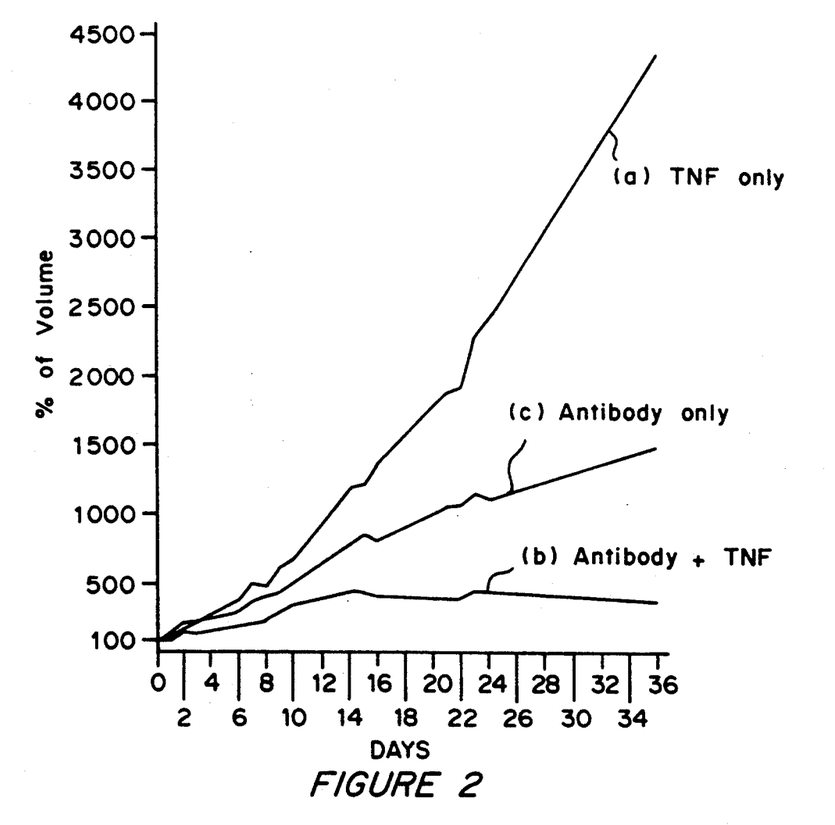
FIG. 2 is a graph of tumor size (% volume) over time (days) following administration of TNF alone (a); anti-Protein C antibody in combination with TNF (b); and anti-Protein C antibody alone (c) to dogs inoculated with the canine veneral tumor.

A second set of dog experiments was then performed and the growth of the tumors followed for an extended period of time. The results are shown in FIG. 2. The conditions and doses of TNF and anti-protein C monoclonal antibody were the same as in the first study. The tumors on dogs treated with the anti-protein C monoclonal antibody alone and the anti-protein C monoclonal antibody-TNF combination both demonstrated a marked decrease in the rate of growth. To monitor histologic changes in the tumors, true cut needle biopsies were performed on day 2 and day 4. Total excision was carried out on day 36. Tissue was examined and compared in regard to lymphocytic infiltrate, spindle cell changes, necrosis and polymorphonuclear leukocytic infiltration. The results are shown in Table I.

TABLE I

| | TUMOR HISTOLOGY | | | | | | | | |
|---|---|---|---|---|---|---|---|---|---|
| | Lymphocytes Day | | | PMN Day | | | Necrosis | | |
| | 2 | 4 | 36 | 2 | 4 | 36 | 2 | 4 | 36 |
| TNF | 1+ | 1+ | 2+ | 1+ | 2+ | 1+ | — | — | 1+ |
| Antibody alone | 4+ | 2+ | 4+ | — | 3+ | 1+ | — | 1+ | 3+ |
| TNF + Antibody | 2+ | 1+ | 4+ | +/— | 3+ | 3+ | — | — | 2+ |

The values range from absent (—) to severe (4+).

There was no single parameter which correlated well with the degree of the tumor growth rate. There was prominent lymphocytic infiltration in dogs treated with anti-protein C monoclonal antibody only and anti-protein C monoclonal antibody-TNF. Necrosis observed was a coagulation type, mostly seen in the center of the tumors, and appeared to better correlate with the size of the tumor. There was proliferation of spindle cells and fibrosis which was slightly prominent in dogs treated with anti-protein C monoclonal antibody or the antibody and TNF. PMN infiltration was seen in all cases. However, in the dog treated with the combination, the infiltration by PMN was rather diffuse and frequently associated with focal necrosis.

One interesting finding was the presence of granulomatous nodules at the periphery of the tumor nodule made up with clusters of degenerating tumor cells at the center surrounded by a zone of histiocytes. These were found only in the dog treated with anti-protein C monoclonal antibody and TNF. This finding is more characteristic of the granulomatous inflammation which occurs in tumors following BCG administration, but which has not been found following TNF treatment of tumors in mice. This suggests that the combination of TNF and protein C blockade may induce a cell-mediated inflammatory reaction in the tumor.

Another finding is a decreased capillary blood supply to the tumors of the dogs which have received protein C blockade, alone or in combination with TNF. Normally, the tumors receive blood via an extensive capillary inflow which originates primarily in the skin and subcutaneous tissues and to a lesser extent from the deeper tissues. In the dogs which were treated with protein C blockade, the vessels entering from the surrounding tissue into the tumors are visibly decreased. There is also a marked reduction in the capillary oozing of blood when these tumor are excised. This raises the possibility that angiogenesis has been decreased in the tumors where Protein C blockade occurred.

Since the histomorphological changes observed at two and four days following protein C blockade do not explain the major differences in tumor growth rate observed in the three animals, the light and electron microscopic characteristics of the tumors at much earlier times were studied. Four dogs with six tumors apiece were treated as follows: 1) placebo, 2) antibody-TNF, 3) TNF, and 4) antibody only. One tumor was removed at −10 min, 10 min, 30 min, 2 hrs, 6 hrs, and 24 hrs from each animal. Representative portions of each tumor were snap frozen in liquid nitrogen for immunohistochemistry, fixed in 3.0% buffered glutaraldehyde for electron microscopy and fixed in 10% buffered formalin for routine histochemical studies.

On light microscopy, a tendency for PMN margination was observed only in the dog treated with the antibody and TNF from the specimen obtained more than 30 min after the treatment. Hemorrhagic necrosis was evident in that tumor at 2 hours. No evidence of thrombosis or infarction was observed in other organs.

EXAMPLE 2

Treatment of an unresectable fibrosarcoma with anti-Protein C and TNF.

A dog having a biopsy-proven fibrosarcoma of the soft pallet growing up into the nasal passages was treated with a single intravenous injection of 10 μg TNF/kg body weight followed by a single injection of 1 mg anti-Protein C (HPC4)/kg body weight. Treatment resulted in significant necrosis and greatly improved the ability of the dog to breath through his nose.

Figures 3A, 3B:
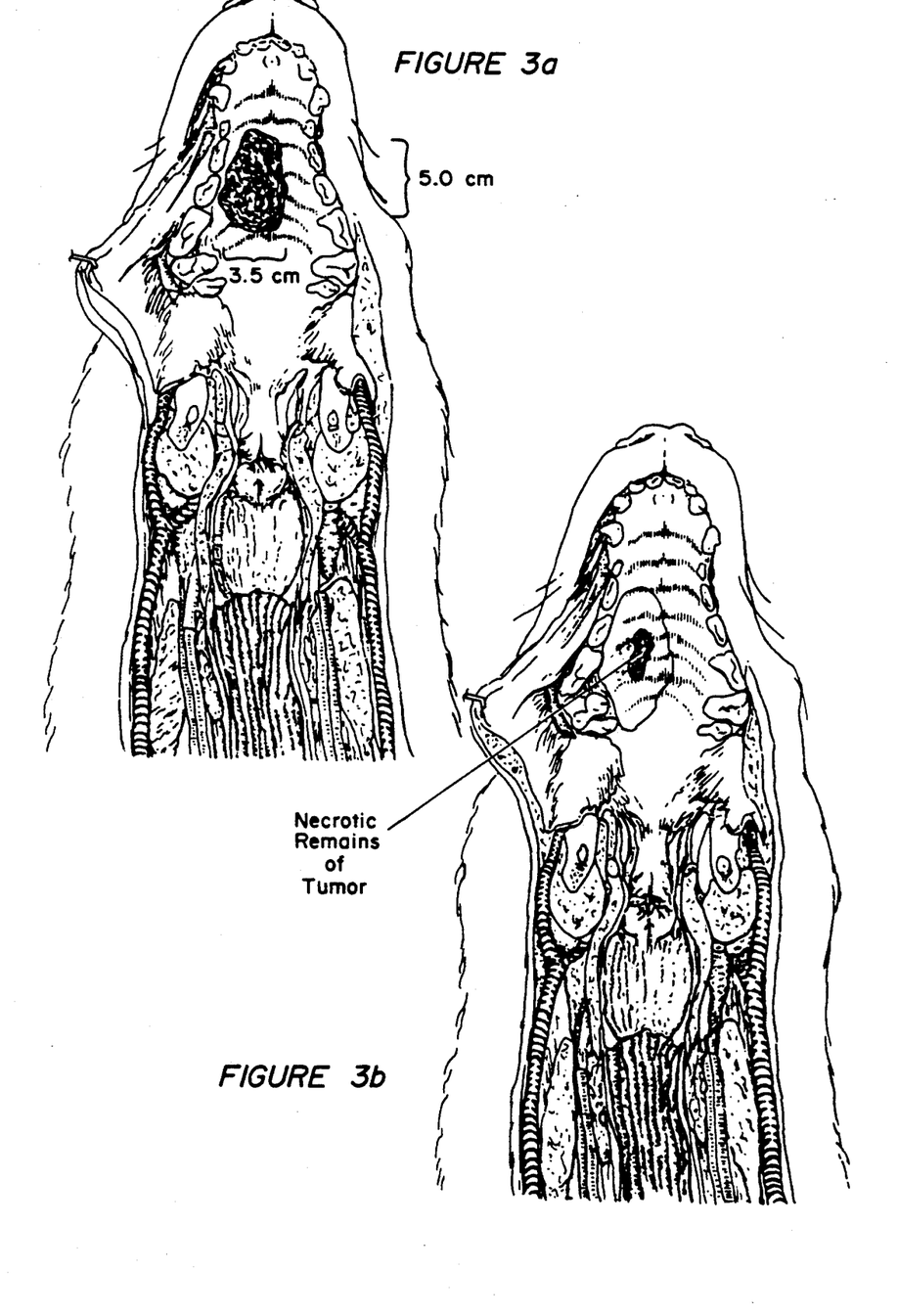
FIGS. 3A and 3B are perspective views of the fibrosarcoma in a dog prior to treatment (FIG. 3A) and eleven days post treatment (FIG. 3B).

The location and the size of the tumor, measuring approximately 3.5 cm×5.0 cm, at the time of treatment is shown in FIG. 3A. The reduction in size after eleven days, with only a small necrotic portion remaining, is shown in FIG. 3B.

EXAMPLE 3

Treatment of an unresectable adenocarcinoma with anti-protein C and TNF.

Figure 4A:
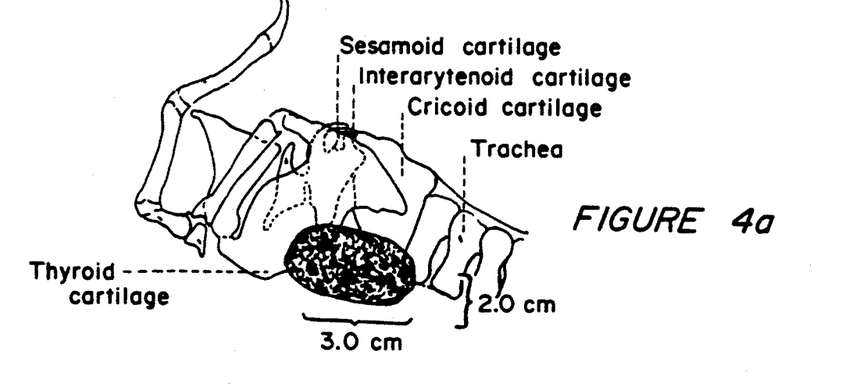
FIGS. 4A and 4B are views of a laryngeal adenocarcinoma in a dog prior to treatment, FIG. 4A in cross-section with the laryngeal cartilages, and FIG. 4B in perspective.
Figure 4B:
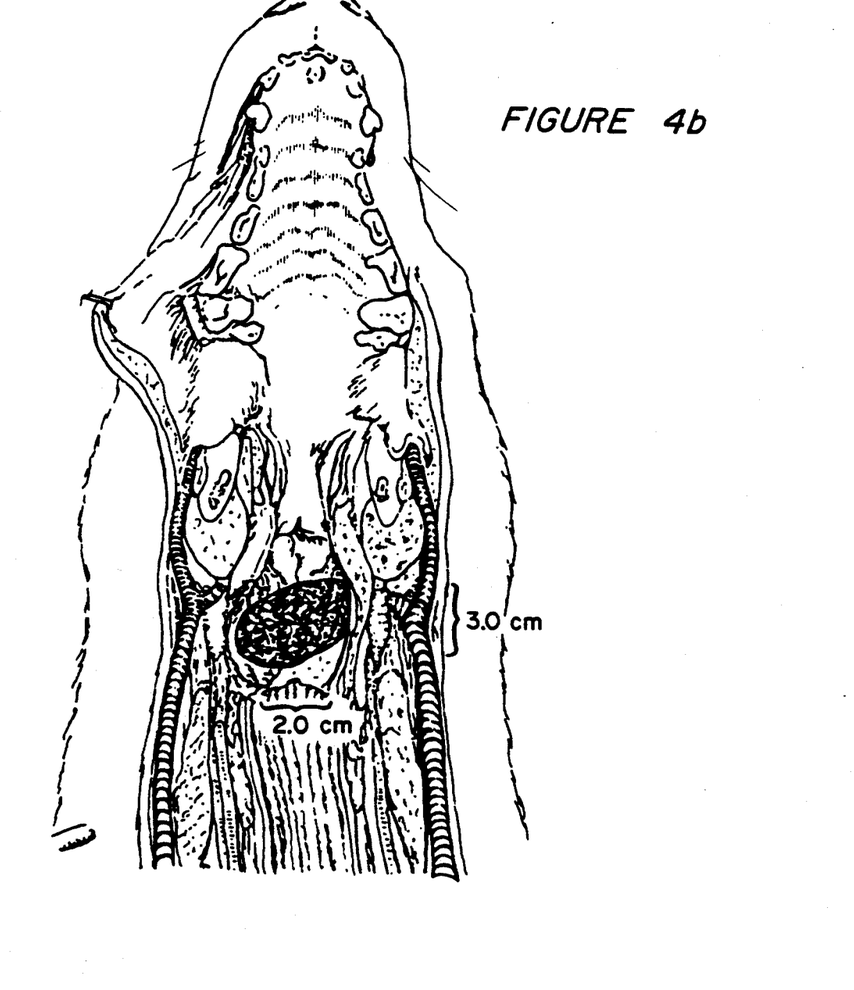

A second dog having a biopsy-proven adenocarcinoma in the laryngeal area was also treated with a single injection of 10 μg TNF/kg body weight followed by one mg anti Protein C (HPC4)/kg body weight. The animal entered the hospital with severe difficulty breathing due to obstruction by the tumor. The tumor measured approximately 3 cm×2 cm by palpation. FIGS. 4A and 4B are views of the laryngeal adenocarcinoma prior to treatment, FIG. 4A in cross-section with the laryngeal cartilages, and FIG. 4B in perspective.

Twelve days following treatment, the tumor volume was reduced 50%. One week later the tumor was no longer detectable. The dog returned to full functional status, is able to bark, and has been walking 4 to 5 miles per day with her owners. At six weeks some detectable tumor mass had reappeared and additional treatment was warranted.

Both animals in examples 2 and 3 tolerated the therapy very well, despite being geriatric cases, both animals being over 10 years of age.

EXAMPLE 4

Treatment of a lymphoma using anti-Protein C and TNF.

A dog With advanced lymphoma was treated with a single administration of TNF and HPC4. No improvement was observed.

EXAMPLE 5

Treatment of Sinclair swine melanoma with TNF, anti-protein C monoclonal antibody, or TNF in combination with anti-protein C.

Sinclair miniature swine spontaneously develop multiple cutaneous melanomas which have the ability to metastasize and regress. These animals are an accepted model for human melanomas because of the many features in common with human melanomas: tumors develop spontaneously; swine possess a wide spectrum of benign melanocyte lesions capable of malignant transformation; melanomas in pigs histopathologically resemble human superficial spreading melanoma; metastatic disease is correlated with deeply invasive cutaneous tumors; the pattern of metastatic spread is analogous to the distribution of metastases in human melanoma (as in human melanoma, the highest incidence of metastasis is to lymph nodes, lungs, and liver, with metastases to multiple organ systems in one-third of the animals); the histopathology of cutaneous regression is similar; a tumor-related immune response occurs in the host; and a genetic component is pigs is comparable to a genetic component of some melanomas in humans. This model is reviewed by Oxenhandler, et al., *Amer. J. Pathol.* 96(3), 707-714 (1979) and Hook, et al., *AJP* 108(1), 130-133 (Jul. 1982).

10 day old 1 kg pigs were treated with either TNF (10 μg TNF/kg body weight/animal), the anti-protein C monoclonal antibody HPC4 (one mg HPC4/kg body weight/animal), or TNF in combination with HPC4 (10 μg TNF/kg body weight followed by one mg HPC4/kg body weight/animal). The compositions were injected in the tissues directly under the melanomas.

The tumor on the pig which received the combination of HPC4 and TNF showed extensive hemorrhage and necrosis. Over a 72 hour period the volume of the tumor was reduced by 80%. There was no reduction in size or necrosis in the tumors treated with either TNF or HPC4 alone.

In summary, the data demonstrates that blocking protein C activation in some tumor-bearing animals, either alone or in combination with cytokine administration, has a marked effect on tumor growth and in some cases results in regression of the tumors. The data consistently shows a large difference between the tumor growth in dogs treated with TNF alone versus antibody alone, and a large difference between TNF only versus antibody and TNF. However, it is not clear if there is a significant difference between the antibody alone and the antibody and TNF treated dogs. The difference in the swine was significant.

It may be possible to optimize the effects of protein C blockade in a number of ways. In the examples, the TNF and antibody were administered within a single 15 minutes period. Based on the potential priming effect, the TNF may have on tumor necrosis, TNF could be administered 6 hours before the protein C blockade to increase tumor damage. Since TNF has a short plasma half-life, subsequent intravenous administration of TNF during the first 18 hours the anti-protein C monoclonal antibody is in the circulation may also be used to increase tumor damage. Prolonged protein C blockade on the tumors, both with and without TNF, may also increase tumor damage, using sequential doses of the anti-protein C monoclonal antibody at 12 hour intervals.

The HPC4 anti-protein C monoclonal antibody preparations are relatively endotoxin-free, but still result in the administration of between 15 ng and 30 ng endotoxin (total dose per dog per experiment) as measured by the Limulus amebocyte lysate assay (Associates of Cape Cod, Inc., Wood Hole). This endotoxin could elicit tumor necrosis factor production in the recipient animals, which may amplify the effect of the antibody administered in the absence of the TNF. Endotoxin can be removed from the anti-protein C monoclonal antibody preparations using immobilized polymyxin B (Pierce Biochemical, Ill.). Anti-protein C monoclonal antibody preparations can also be filtered on G-200 Sephadex to remove any possible microaggregates immediately before infusion, which may be cleared more rapidly than non-aggregated antibody.

A single infusion of anti-protein C monoclonal antibody has a significant effect on tumor growth in preliminary studies. Repeated infusions of the anti-protein C monoclonal antibody over a period of 5 days may be more effective in blocking tumor growth than a single administration of the antibody. Sufficient anti-protein C monoclonal antibody should be employed to keep plasma levels of the antibody over 10 μg/ml. Dog protein C levels range from 3-5 μg/ml, as measured by Laurell rocket electrophoresis using goat anti-dog protein C. This level of anti-protein C monoclonal antibody should be adequate to block all protein C activation assuming that a 1:1 stoichiometric complex forms between the monoclonal antibody and the canine protein C.

To determine if adequate quantities of the monoclonal antibody have in fact been administered to complex all circulating canine protein C, aliquots of heparinized plasma can be passed over a column of the anti-protein C monoclonal antibody (HPC4) immobilized on Affigel-10 (Bio-Rad Laboratories, Calif.). The immobilized antibody binds to free protein C, but not to activated protein C or circulating protein C—antibody complex. The column bound protein C can be quantitated as previously described by Vigano D'Angelo, S., Comp, P. C., Esmon, C. T., et al. *J.Clin.Invest.* 77,416-425 (1986). An alternative approach is to remove the antibody-protein C complex from the plasma with an immobilized polyclonal antibody directed against the antibody. The residual free protein C can then be quantitated by Laurell rocket electrophoresis, or if increased sensitivity is required, by a radioimmunoassay.

The natural fibrinolytic system in dogs is very potent and may be capable of lysis of microvascular thrombi, thereby serving to protect the tumors from blockade of the protein C system. This can be blocked by administration of an inhibitor such as epsilon-amino caproic acid (EACA) before and following the administration of the anti-protein C monoclonal antibody. EACA is rapidly secreted into the urine and therefore will be given intravenously at one-hour intervals for 12 hours. The effect of EACA can be monitored by the euglobulin clot lysis time method described by Comp, P. C. and Esmon, C. T. The Regulation of Coagulation, edited by Mann, K. G. and Taylor Jr., F. B., p. 583-588 (Amsterdam: Elsevier North-Holland, 1980z0. EACA may enhance the anti-tumor effects of the anti-protein C monoclonal antibody.

The role of platelets in the tumor directed effects of the anti-protein C monoclonal antibody is difficult to assess. A preliminary survey of the electron microscopic data at two hours after protein C blockade indicate that platelets are not present in the fibrin deposition in the tumor capillaries of the animals receiving the anti-protein C monoclonal antibody. The fibrin strands which are observed appear to be closely associated with the endothelial surface. This suggests that the endothelial surface may be capable of serving as a site of clot initiation under these conditions. This is consistent with the observation of fibrin directly associated with the vessel wall in rabbits infused with interleukin-1, described by Nawroth, P. P., Handley, D. A., Esmon, C. T., et al. *Proc.Natl.Acad.Sci. USA* 83,3460-344 (1986). If platelets are necessary for the effects of the anti-protein C monoclonal antibody on the tumors, thrombocytopenia may protect the tumor from the protein C blockade.

Modifications and variations of the compositions and methods for treatment of tumors by blocking the protein C coagulation system will be obvious to those skilled in the art from the foregoing detailed description of the invention. Such modifications and variations are intended to come within the scope of the appended claims.

We claim:

1. A composition for inhibition of tumor growth in a patient comprising:
a pharmaceutical carrier containing a compound to block the protein C anticoagulation system selected from the group consisting of anti-protein C antibodies, anti-protein S antibodies, inactivated protein C and C4b binding protein in combination with a cytokine selected from the group consisting of tumor necrosis factor and a cytokine eliciting expression of tumor necrosis factor, wherein the combination is in an effective dosage to cause hemorrhagic necrosis of the tumor and the dosage of the cytokine in the combination is not effective in the absence of the protein C blocking compound.

2. The composition of claim 1 wherein the Protein C blocking compound is an anti-Protein C antibody.

3. The composition of claim 1 wherein the cytokine stimulates natural killer and lymphokine-activated killer cell-mediated cytotoxicity.

4. The composition of claim 1 wherein the cytokine is selected from the group consisting of tumor necrosis factor, gamma interferon, granulocyte-macrophage colony stimulating factor, interleukin-1 and interleukin-2.

5. The composition of claim 1 further comprising a chemotherapeutic agent selectively inhibiting growth of rapidly replicating cells.

6. The composition of claim 1 further comprising endotoxin in a dosage stimulating production of tumor necrosis factor.

7. The composition of claim 1 in combination with a source of radiation causing inflammation of the tumor.

8. The composition of claim 1 in combination with a chemotherapeutic agent inhibiting replication of cells.

9. The composition of claim 4 comprising anti-Protein C antibodies in a dosage equal to or greater than the molar concentration of Protein C in the blood of the patient and tumor necrosis factor in a dosage delivering less than 100 $\mu$g TNF/kg body weight.

10. The composition of claim 4 comprising anti-Protein S antibodies in a dosage equal to or greater than the molar concentration of Protein S in the blood of the patient and tumor necrosis factor in a dosage delivering less than 100 82 g TNF/kg body weight.

11. The composition of claim 4 comprising C4b binding protein in a dosage equal to or greater than five times the molar concentration of C4b binding protein in the blood of the patient and tumor necrosis factor in a dosage delivering less than 100 $\mu$g TNF/kg body weight.

12. A method for inhibition of tumor growth in a patient comprising: administering to a patient having a tumor a compound specifically blocking protein C, wherein the compound is not a cytokine, in a dosage blocking the Protein C anticoagulation system and facilitating hemorrhagic necrosis of microvasculated solid tumors.

13. The method of claim 12 further comprising selecting the Protein C blocking compound from the group consisting of anti-Protein C antibodies, anti-Protein S antibodies, inactivated activated Protein C and C4b binding protein.

14. The method of claim 12 further comprising administering a cytokine selected from the group consisting of tumor necrosis factor and a cytokine eliciting expression of tumor necrosis factor, wherein the combination of protein C blocking agent and cytokine is administered in a dosage causing hemorrhagic necrosis of the tumor.

15. The method of claim 14 wherein the cytokine is selected from the group consisting of tumor necrosis factor, gamma interferon, granulocyte-macrophage colony stimulating factor, interleukin-1 and interleukin-2.

16. The method of claim 12 further comprising providing endotoxin in a dosage stimulating production of tumor necrosis factor.

17. The method of claim 13 wherein the Protein C blocking compound is anti-Protein C and the anti-Protein C is administered in a dosage equal to or greater than the level of Protein C in the blood.

18. The method of claim 17 wherein the dosage is equal to or greater than approximately 10 μg antibody/ml of blood.

19. The method of claim 13 wherein the Protein C blocking compound is C4b binding protein and the C4b binding protein is administered in a dosage equal to or greater than five times the plasma levels of C4b binding protein.

20. The method of claim 13 wherein the Protein C blocking compound is anti-Protein S and the anti-Protein S is administered in a dosage equal to or greater than the level of Protein S in the blood.

21. The method of claim 20 wherein the dosage is equal to or greater than approximately 10 μg antibody/ml of blood.

22. The method of claim 14 wherein the Protein C blocking compound and the cytokine are administered to the tumor.

23. The method of claim 14 further comprising administering a chemotherapeutic agent selectively inhibiting growth of rapidly replicating cells.

24. The method of claim 14 further comprising irradiating the patient to cause inflammation of the tumor.

25. The method of claim 14 further comprising using hyperthermia to cause inflammation of the tumor.

26. The method of claim 14 wherein the Protein C blocking compound and cytokine are administered intravenously.

27. The method of claim 14 wherein the Protein C blocking compound and cytokine are administered in a single dosage.

28. The method of claim 12 further comprising administering a compound inhibiting blocking of the Protein C system by the blocking agent.

29. The method of claim 28 wherein the inhibitory compound is selected from the group consisting of Protein C, activated Protein C, Protein S, and active site inactivated factor Xa.

* * * * *